(12) United States Patent
Klee et al.

(10) Patent No.: US 6,493,639 B1
(45) Date of Patent: Dec. 10, 2002

(54) METHODS FOR SAMPLE IDENTIFICATION USING PATTERN RECOGNITION UNDER LOCKED CONDITIONS

(75) Inventors: Matthew S. Klee, Wilmington, DE (US); Bruce D. Quimby, Lincoln University, PA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/571,217

(22) Filed: May 16, 2000

(51) Int. Cl.[7] .............................................. G06F 19/00
(52) U.S. Cl. ......................................... 702/22; 436/161
(58) Field of Search .................. 436/161, 89; 702/20, 702/23.26; 73/23.26, 23.4; 210/198.2

(56) References Cited

U.S. PATENT DOCUMENTS

| | | | |
|---|---|---|---|
| 3,991,626 A | * 11/1976 | Shair | 73/23.4 |
| 4,852,017 A | * 7/1989 | Hunkapiller | 702/20 |
| 5,827,946 A | * 10/1998 | Klee et al. | 73/23.26 |
| 6,153,438 A | * 11/2000 | Blumberg et al. | 436/161 |
| 6,289,287 B1 | * 9/2001 | Meng et al. | 702/23 |

* cited by examiner

*Primary Examiner*—Kamini Shah
*Assistant Examiner*—Xiuquin Sun

(57) ABSTRACT

A preferred method for identifying analytes of samples by utilizing chemometric analysis for interpreting chromatographic data obtained under locked conditions includes the steps of: (1) providing a locking GC system which includes a column operated at a column head pressure; (2) adjusting the column head pressure of the locking GC system so that a column void time of the column in the locking GC system, when a known analyte is eluted therethrough, is matched with the column void time of the column in a reference GC system, when the known analyte is eluted therethrough; (3) analyzing the sample with the locking GC system so that chromatographic data corresponding to the sample is compiled, and; (4) performing chemometric analysis on the chromatographic data.

34 Claims, 7 Drawing Sheets

REQUIRED PRESSURE CHANGE
=
(ACTUAL RT - TARGET RT) / ( $\Delta P/\Delta T$ )

METHODS FOR SAMPLE IDENTIFICATION USING PATTERN RECOGNITION UNDER LOCKED CONDITIONS

BACKGROUND OF THE INVENTION

1. Field of the Invention

The present invention generally relates to chromatographic analysis and, in particular, to methods for classifying samples by utilizing chemometrics analysis for interpreting chromatographic data obtained under locked conditions.

2. Description of the Related Art

Gas chromatography is a method for analyzing a sample of interest, which may include one or more analytes, to qualitatively determine the identity of the analytes as well as to quantitatively determine the concentration of each of the analytes. This analysis also may include comparing the sample of interest to previously analyzed samples for the purpose of classifying the sample of interest. Gas chromatography typically involves a series of steps, including: sample collection, sample preparation, sample introduction into a chromatographic or separation column, chromatographic separation of the sample into individual analytes, detection of those analytes, and data acquisition and reduction. As is well known, the step of data reduction, which enables the identification of the analytes present in the sample, can be a complex task, primarily due to the multivariate nature of the acquired data.

Chemometrics is a general term applied to the use of statistics and mathematics to extract meaningful information from multivariate data. In a representative implementation, statistical algorithms may be employed to help one reduce large amounts of data into a small number of salient descriptors. Chemometrics typically is applied for one or more of the following primary purposes: (1) to interrogate data efficiently (trend analysis, correlation of results, outlier identification, identification of significant variables, etc.); (2) to track data or a measurement function on an on-going basis (control charting, limit detection); (3) to quantify results based on multivariate response (complex calibration/response functions), and; (4) to reduce complex (e.g., multivariate or multiple response) measurements into classes of like results (classification).

In the context of chromatography, chemometrics may be utilized to provide pattern recognition functionality for interpreting acquired chromatographic data and tends to be most effective when variability in retention times of samples eluting through the separation column of a gas chromatograph is minimized. Heretofore, variability in retention times typically has been addressed by applying a post-analysis adjustment to acquired chromatographic data, such as by mathematically "aligning" the chromatographic time scales of chromatograms relating to multiple samples. However, post-analysis mathematical approaches for "aligning" chromatograms include inherent weaknesses, such as requiring reference peaks or patterns to be present in the data for automatic adjustment to work consistently. This may require adding compounds to each sample (internal standards) and also may lead to errors because samples of unknown composition can vary widely in the response or ratio of response of peaks, thereby potentially leading to incorrect assignment of reference peaks or patterns.

Additionally, typical post-analysis mathematical adjustment of acquired data can not compensate for changes in the order of elution of peaks that can result from operation of GC systems under unlocked conditions. Thus, even if reference peaks are identified and the time axis of the chromatographic data is adjusted for an overall improvement, the retention times of several key individual peaks may still be incorrect (possibly even worse than before the adjustment), potentially resulting in the incorrect classification of the resulting "adjusted" patterns.

Therefore, there exists a need for improved methods which address these and other shortcomings of the prior art.

SUMMARY OF THE INVENTION

Briefly described, the present invention relates to methods for analyzing samples by utilizing chemometric analysis for interpreting chromatographic data obtained under locked conditions. A preferred method comprises the steps of: (1) providing a locking GC system which includes a column operated at a column head pressure; (2) adjusting the column head pressure of the locking GC system so that a column void time of the column in the locking GC system, when a known analyte is eluted therethrough, is matched with the column void time of the column in a reference GC system, when the known analyte is eluted therethrough; (3) analyzing the sample with the locking GC system so that chromatographic data corresponding to the sample is compiled, and; (4) performing chemometric analysis on the chromatographic data.

Alternatively, the column head pressure of the locking GC system may be adjusted so that a retention time of the known analyte in the column of the locking GC system is matched with the retention time of the known analyte in the column of the reference GC system.

In accordance. with another aspect of the present invention, an alternative embodiment for chromatographically analyzing a sample comprises the steps of: (1) receiving chromatographic data from a locking GC system; and (2) performing chemometric analysis on the chromatographic data.

Other objects, features, and advantages of the present invention will become apparent to one with skill in the art upon examination of the following drawings and detailed description. It is intended that all such objects, features, and advantages be included herein within the scope of the present invention, as defined in the appended claims.

BRIEF DESCRIPTION OF THE SEVERAL VIEWS OF THE DRAWINGS

The present invention, as defined in the claims, can be better understood with reference to the following drawings. The drawings are not necessarily to scale, emphasis instead being placed on clearly illustrating the principles of the present invention. In the drawings:

DETAILED DESCRIPTION OF THE PREFERRED EMBODIMENT

Figure 1:
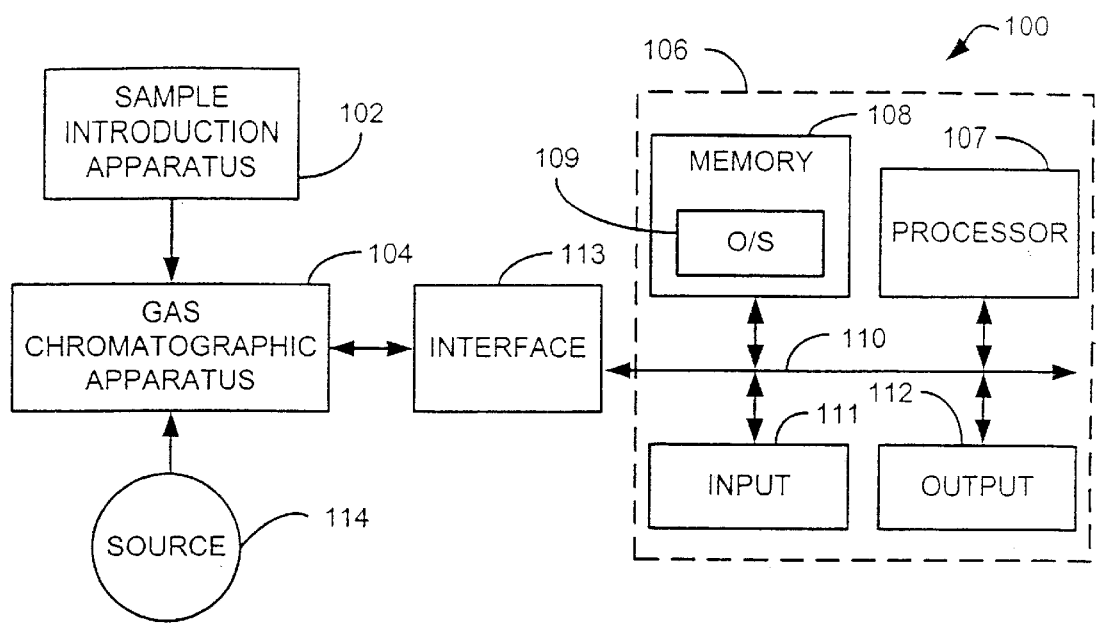
FIG. 1 is a schematic diagram of a representative GC system.

Reference will now be made in detail to the description of the invention as illustrated in the drawings, with like numerals indicating like parts throughout the several views. As shown in FIG. 1, a representative analytical instrument system 100, which may utilize a preferred method of the present invention, includes a sample introduction apparatus 102, a chromatographic apparatus 104 and a computing apparatus 106. Computing apparatus 106 generally comprises a processor 107 and a memory 108 with an operating system 109. Herein, the memory 108 may be any combination of volatile and nonvolatile memory elements, such as random access memory or read only memory. The processor 107 accepts instructions and data from memory 108 over a local interface 1 10, such as a bus(es). Computing apparatus 106 also includes an input device(s) 111 and an output device(s) 112. Examples of input devices may include, but are not limited to a serial port, a scanner, or a local access network connection. Examples of output devices may include, but are not limited to, a video display, a Universal Serial Bus, or a printer port. Generally, computing apparatus 106 may run any of a number of different platforms and operating systems, including, but not limited to, Windows NT™, Unix™, or Sun Solaris™ operating systems. Additionally, an interface 113 is provided for interfacing chromatographic apparatus 104 and computing apparatus 106. A source of carrier gas 114, such as hydrogen, nitrogen, or helium, for example, depending upon the particular chromatographic separation to be performed, also is provided.

Figure 2:
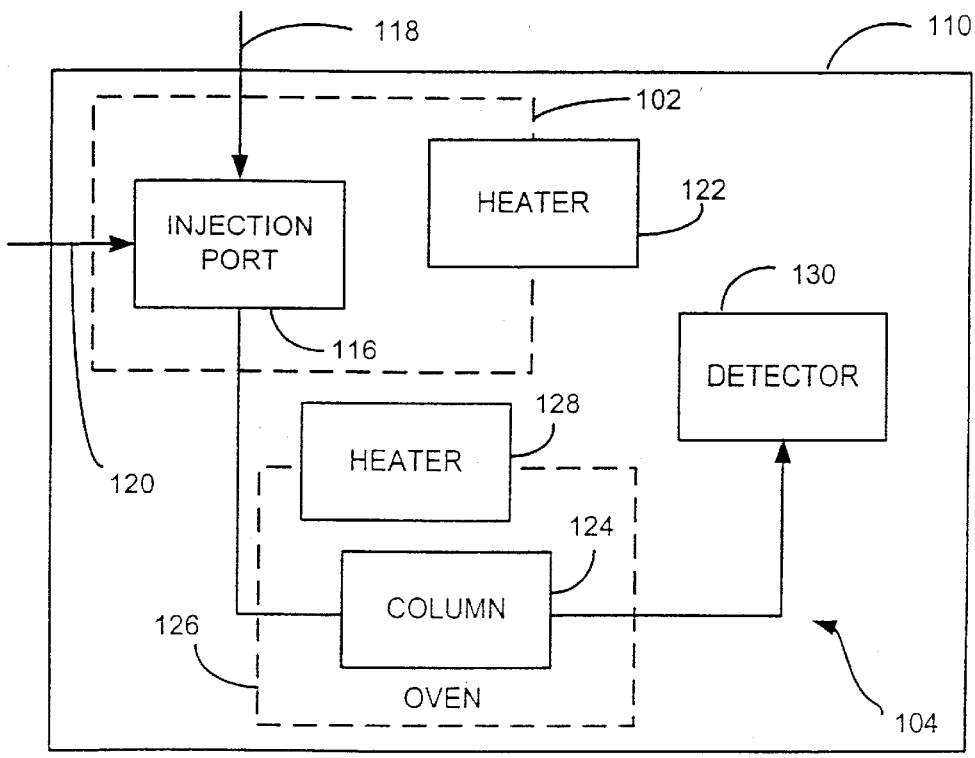
FIG. 2 is a schematic diagram of the representative GC system of FIG. 1.

As shown in greater detail in FIG. 2, analytical instrument system 100 and, more specifically, sample introduction apparatus 102 preferably incorporates an injection port 116 which is adapted to receive a sample, represented by arrow 118, and a flow of carrier gas, represented by arrow 120. Additionally, sample introduction apparatus 102 may incorporate a heater 122 for heating the sample to a desired temperature.

In order to perform a chromatographic separation of a sample, a quantity of the sample typically is injected into the flow of carrier gas, preferably provided in the form of a pressurized stream. The sample introduction apparatus 102 then provides at least a portion of the sample/carrier gas mixture to a separation column 124. Preferably, column 124 is positioned within a chamber or oven 126 which is temperature controlled by one or more heaters 128. In order to ensure that the temperature within the oven 126 is maintained at a desired level, temperatures produced by the heater 128 may be controlled by the computing apparatus 106 (FIG. 1). Thus, the sample/carrier gas mixture provided to the column 124 may be exposed to a controlled temperature profile.

As the sample/carrier gas mixture exits separation column 124, the presence of one or more analytes may be detected by detector 130. Detector 130 generally refers to a physiochemical data output means and, in particular, to means for providing sample peak data representative of information useful as a chromatogram. The detector 130 may include one or more of a wide variety of useful chromatographic detectors, such as flame ionization detectors (FID), photoionization detectors (PID), nitrogen phosphorus detectors (NPD), flame photometric detectors (FPD), thermal conductivity detectors (TCD), atomic emission detectors (AED), electrolytic conductivity detectors (ELCD), electron capture detectors (ECD), mass spectral detectors, and infrared spectral detectors, for example, and is typically also heated.

Typically, a detector output signal is provided to computing apparatus 106 (FIG. 1), and optionally stored in the memory 108. Preferably, the detector output signal is provided in the form of data representative of a series of characteristic peaks in at least one characteristic peak series (known as a chromatographic fingerprint). Preferably, each sample-specific characteristic peak series is then analyzed with the aid of a peak identification method, which will be described in detail hereinafter.

As mentioned hereinbefore, the present invention provides systems and methods for identifying characteristics of samples by utilizing pattern recognition techniques for interpreting chromatographic data obtained under locked conditions. As utilized herein, "locked conditions" refers to conditions present in a gas chromatograph (GC) system which has been tuned or "locked" to parameters embodied in a retention or fingerprint database, i.e., a fingerprint database based on retention times or retention factors. Unknown samples of interest analyzed with a GC system locked to such a database have an increased probability of being identified/classified by direct comparison of certain parameters. For example, when utilizing a GC system which has been retention time locked to a retention time or fingerprint database, unknown samples of interest analyzed on the locked GC system have an increased probability of being identified/classified. In particular, locked retention times provide for very precise patterns and very precise patterns provide for easier differentiation of fingerprints. Likewise, when utilizing a GC system that has been retention factor locked to a retention factor or fingerprint database, unknown samples of interest analyzed on the locked GC system have an increased probability of being correctly identified/classified. Locking the GC system not only ensures that the retention time of the overall chromatogram (the general chromatographic pattern or fingerprint) matches the locked reference data set, but also ensures identical elution order compared to the locked reference set. In this manner, the accuracy and precision of the chromatographic patterns specific to each sample are significantly improved, which, in turn, improves the quality of sample identification/classification.

A GC fingerprint database is created under locked conditions by adjusting the column head pressure of a reference GC system so that the column void time or the retention time of a known analyte equals a defined value. A series of standards are injected into the reference GC system to form the reference database. To ensure that the reference GC system remains locked during development of the database, the column head pressure is periodically adjusted so that the column void time or the retention time of the known analyte remains at the defined value. The developed database then may be stored on a memory storage device and may be accessed for analysis in numerous manners, as described hereinafter.

Several methods for calculating an adjustment to the column head pressure required to retention time lock a GC system are fully disclosed in commonly assigned U.S. patent application Ser. No. 08/728,868, filed on Oct. 10, 1996, entitled "Automated Retention Time Locking" and which is incorporated by reference herein. In particular, the column head pressure of the locking GC system may be adjusted so that column void time of the GC system is matched to the column void time of the column employed for generating the retention time or fingerprint database.

Figure 3:
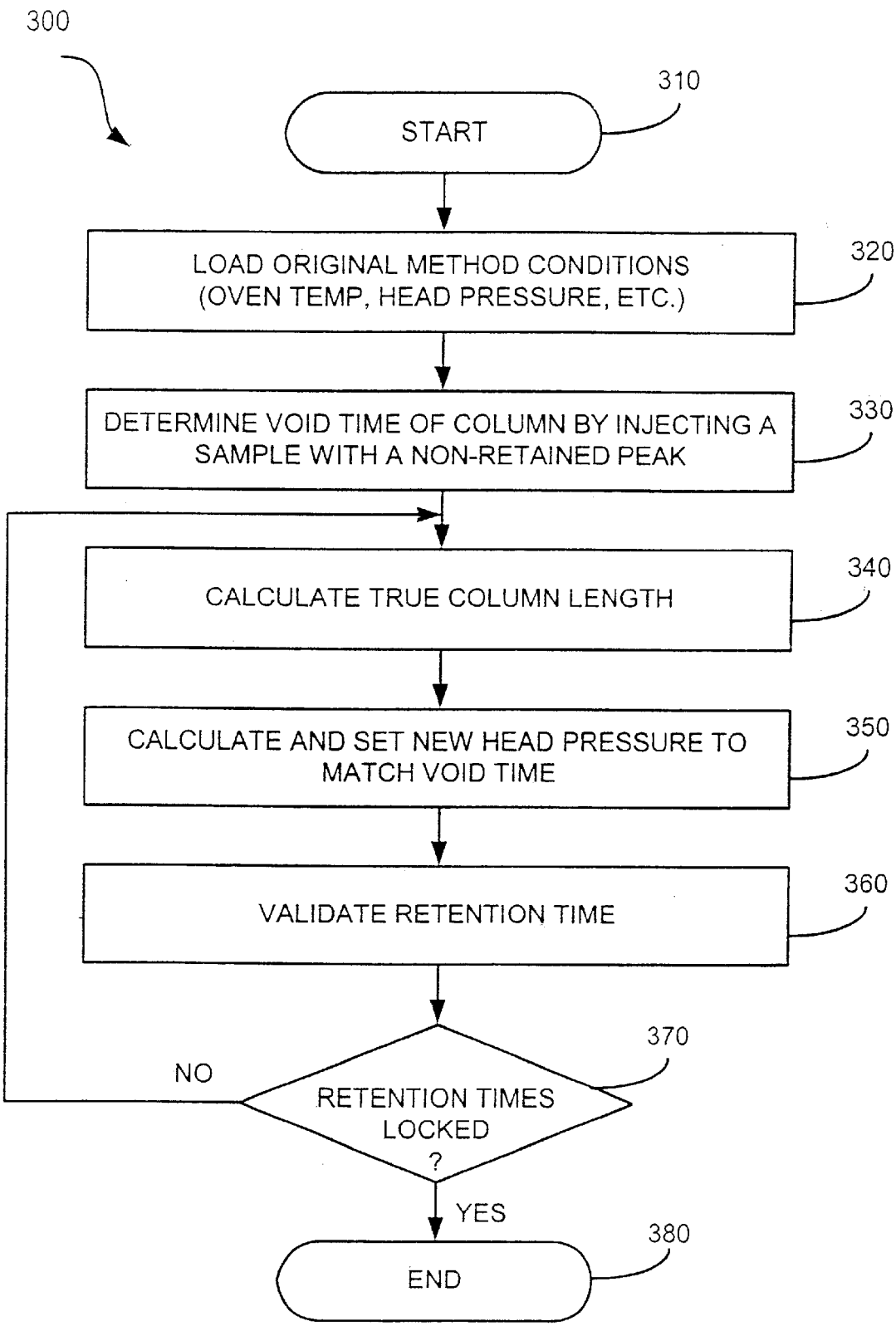
FIG. 3 is a flow diagram depicting the functionality of a preferred method of the present invention.

FIG. 3 depicts a flowchart 300 highlighting representative method steps for retention time locking through matching of column void times. As depicted therein, the method starts at block 310 and then proceeds to block 320, wherein original method conditions for the GC system to be locked are loaded. At block 330, void time of the column of the GC system is determined by injecting a sample with a non-retained peak, and then (at block 340) true column length preferably is calculated, such as by utilizing a flow calculator or GC method translator, for example. Proceeding to block 350, a new head pressure is calculated and set at the GC system to be locked so that the void time matches the void time of the GC system which was utilized to establish the retention time database. At block 360, the new column retention time is validated by injecting a standard and then comparing the retention time of the standard to the desired retention time. At block 370, a determination is made as to whether the GC system has been locked. If it is determined at block 370 that the retention times are not locked within expected tolerance, the method preferably returns to block 340, and then proceeds as described hereinbefore.

Figure 4:
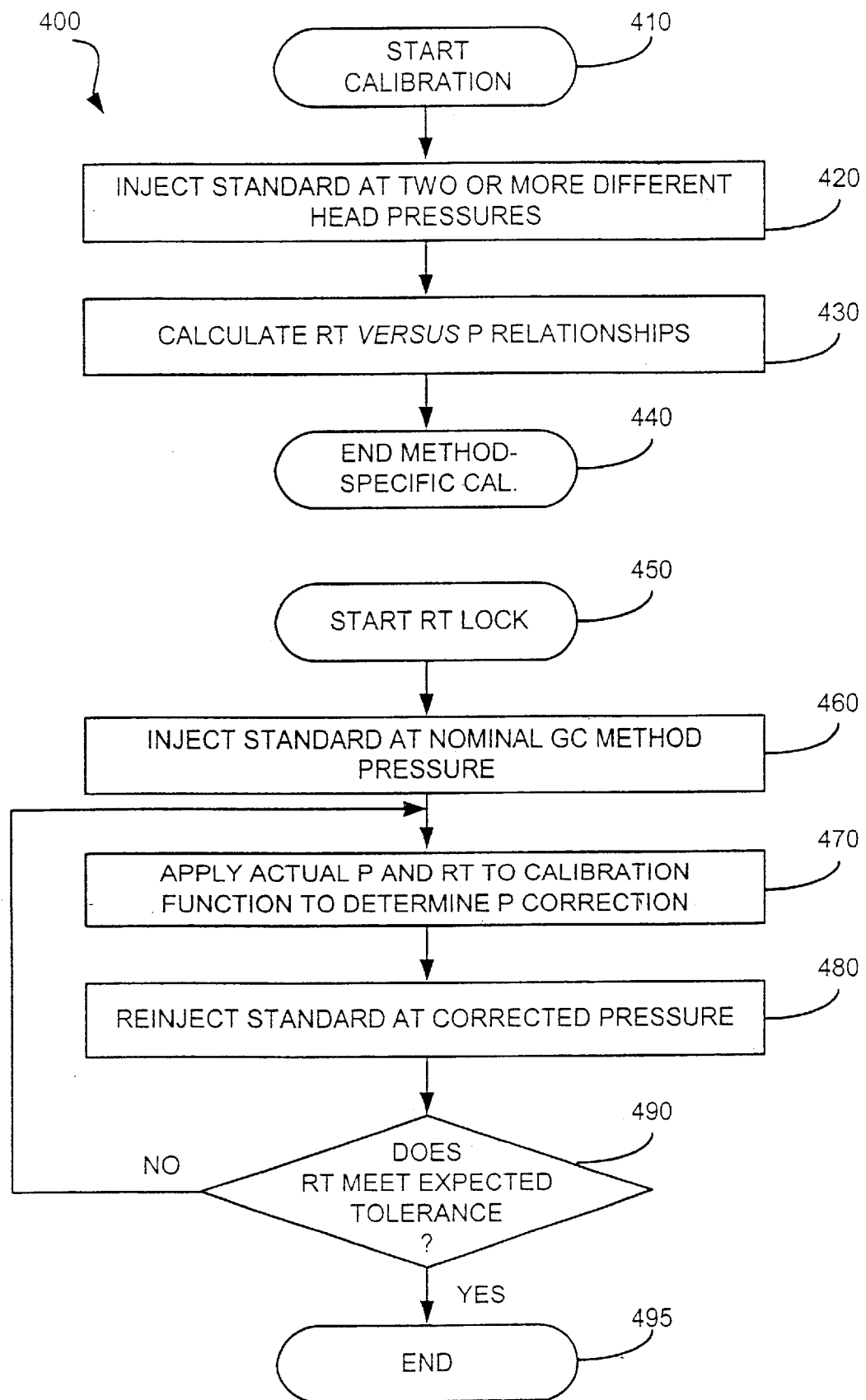
FIG. 4 is a flow diagram depicting the functionality of a preferred method of the present invention.

An alternative method, such as illustrated in FIG. 4, for locking a GC system starts at block 410 and then proceeds to block 420, wherein a known analyte or "standard" having one or more known or "reference" analytes is injected multiple times into the GC system to be locked, e.g., one or more times at a column head pressure above a nominal pressure, and one or more times at a column head pressure below a nominal pressure. At block 430, retention time (RT) versus head pressure (P) relationships are calculated, and form the basis of a method-specific locking calibration. Subsequently, to lock a given GC system using the locking calibration, one injects a sample or standard containing the same reference analyte(s) as that used for the locking calibration at nominal method pressure (block 460). Then (block 470) the actual measured retention time(s) and head pressure are applied to the locking calibration such that a pressure correction is determined. The corrected pressure is set and the sample/standard is reinjected (block 480) to validate that the GC system is locked. If it is determined, such as in block 490, that further adjustment is necessary to meet expected retention time tolerance, the system may return to block 470, and proceed as described hereinbefore; otherwise, the method preferably ends at block 495.

The following formula may be employed for calculating a head pressure adjustment where a GC system to be locked employs column and operating parameters that are not different than those employed for generating the retention time or fingerprint database:

$$\text{Pressure Adjustment} = (RT_n - RT_{TARGET})/(\Delta RT/\Delta P).$$

Figure 5:
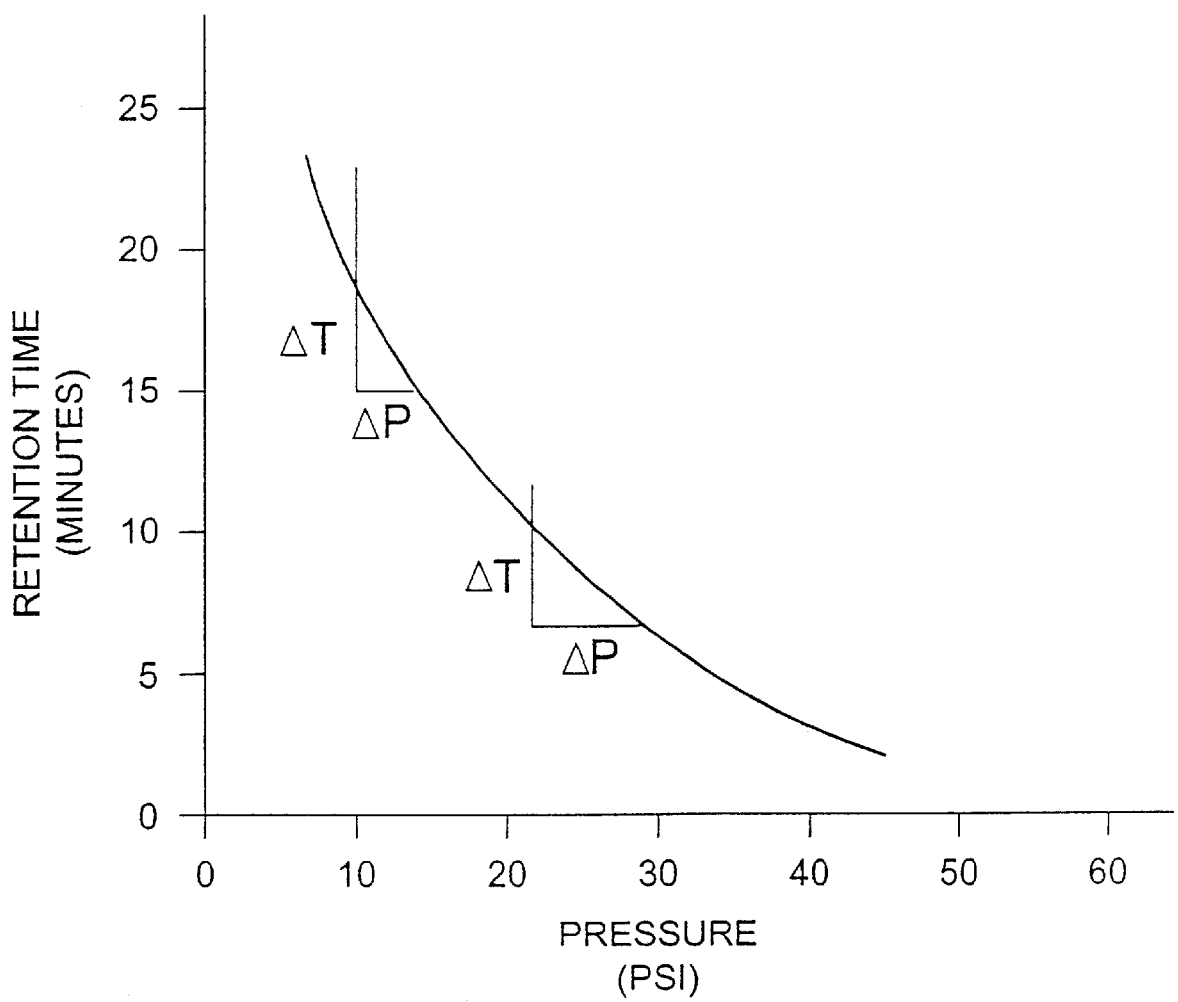
FIG. 5 is a graph depicting retention time versus pressure.

Representative required pressure changes calculated with the aforementioned formula are depicted in FIG. 5.

Notwithstanding the ability for the empirical locking calibration process to compensate for variations in column and operational parameters, effective operation of a GC system in retention time locked mode requires precise oven temperature control, stable stationary phase chemistry and film thickness, and precise column head pressure control. Precision of oven temperature control directly impacts precision of retention times. An example of an excellent oven design is exemplified in U.S. Pat. No. 4,181,613, issued on Jan. 1, 1980 to Welsh et. al., which is incorporated by reference herein, although various other oven designs may be utilized. While temperature offset of only 0.1 degree centigrade may result in a retention time shift, retention time locking may accurately compensate for temperature offsets of at least 5 degrees centigrade and may still maintain a retention time lock of within 0.1 minute (6 seconds). While increasingly greater temperature shifts also can be compensated for, variations in the retention times of some solutes will tend to deviate from original values by amounts greater than 0.1 minute, which, in turn, requires increased retention time windows and correspondingly lower quality chemometric results.

Identification of column parameters (dimensions, film thickness, and stationary phase type) facilitates RT locking based on void time adjustment, since this is based on theoretical mathematical functions. The column parameters necessary for submission to the mathematical functions can be obtained by proper column selection prior to installation within the locking GC system and through various known calibration procedures. For example, the Agilent Technologies, Inc. 6890 GC has a "column calibration" function based on some user inputs, can calculate the inside diameter of the column and the column length.

Alternatively, one can use the empirical locking calibration process (FIG. 4) which does not require extremely accurate column parameter information to lock a given GC system. This approach has further benefits compared to the theoretical-based void time approach in that it can compensate for some deviations in individual phase thickness, column length, column diameter and oven temperature offset from those in the nominal method.

Precise column head pressure control may be provided by electronic pressure control, such as set forth in U.S. Pat. No. 4,994,096, issued on Feb. 19, 1991 to Klein et al., and which is incorporated by reference herein.

In a manner similar to that described in relation to the development of a retention-time type fingerprint database based on absolute retention times, a retention-factor type fingerprint database based on retention factors may be created by including the additional step of calculating a retention factor (k) for the chromatographic peaks by utilizing the following:

$$k = (RT - VT)/VT$$

where VT is the column void time and RT is the retention time of an analyte through the column of the reference GC system. The resultant retention factor data is then stored in a retrievable database. Such a method for developing a retention factor database is fully disclosed in commonly assigned U.S. patent application Ser. No. 08/859,630, filed on May 20, 1997, entitled "Retention Factor Database" and which is incorporated by reference herein. A desirable consequence of operating in the locked retention factor mode is the ability to generate chromatographic fingerprints and chemometric models based on retention factors. This, in turn, provides a more flexible database with which to identify/classify samples.

As described briefly hereinbefore, chemometrics analysis may be utilized to provide statistical and mathematical tools for interpreting acquired chromatographic data.

In this regard, there are a variety of useful approaches to chemometrics, with the best approach for a given task depending on the type of data and the type of information being sought. The following are examples of such approaches: (1) Exploratory Data Analysis—the computation and graphical display of patterns of association in multivariate data sets, where the chemometric algorithms are designed to reduce large and complex data sets into a set of "best views" of the data. Two commonly utilized exploratory data analysis techniques are PCA (Principal Component Analysis) and HCA (Hierarchical Cluster Analysis). (2) Classification Analysis—the computation and graphical display of class assignments based on the multivariate similarity of one sample to others, where the chemometric algorithms are designed to compare unknown samples to a previously analyzed "training" set. Two commonly utilized classification analysis techniques are SIMCA (Soft Independent Modeling Class Analogy) and KNN (K-Nearest Neighbors). (3) Regression Analysis—typically used when a property of interest is difficult to measure directly, or if the measurement is multivariate in nature. Regression methods can be used to determine the mathematical correlations that yield the best calibration function. Two commonly utilized regression analysis techniques are PLS (Partial Least Squares) and PCR (Principal Component Regression).

There are several software packages currently available that contain a core set of the above capabilities as well as preliminary data manipulation routines to prepare acquired chromatographic data for submission to chemometric analysis. Representative examples of such software packages include Pirouette™ from Infometrix, Inc. of Woodinville, Wash., and MATLAB™ from The MathWorks of Natick, Mass., although various other applications may be utilized.

Figure 6:
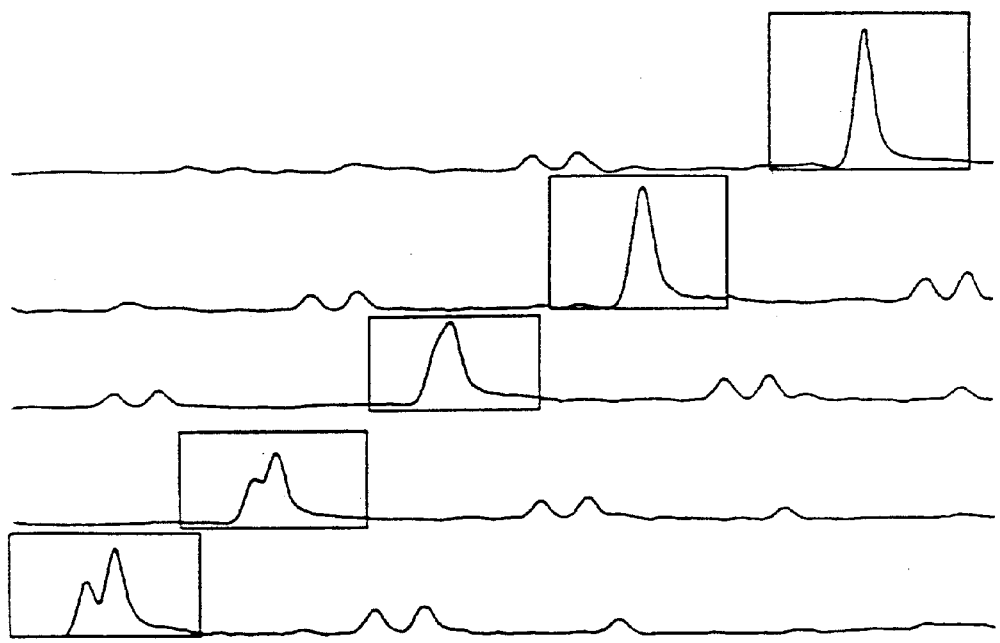
FIG. 6 depicts representative chromatograms generated by unlocked GC systems.
Figure 7:
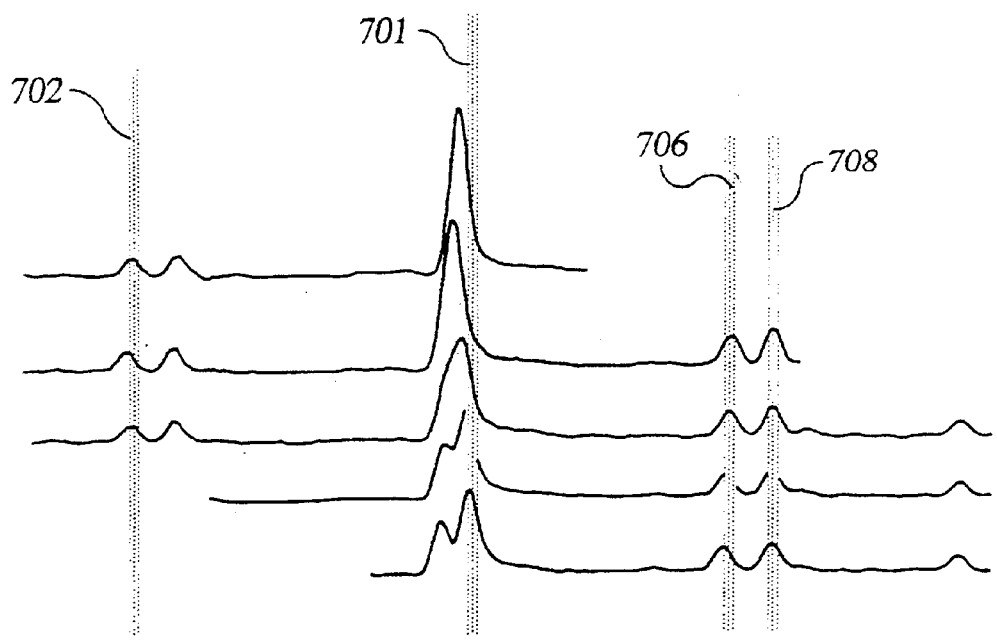
FIG. 7 depicts the representative chromatograms of FIG. 6 after post-analysis processing whereby typical mathematical alignment approaches were employed.

Referring now to FIGS. 6 and 7, representative disadvantages of utilizing unlocked GC systems are presented. As depicted in FIG. 6, repeat analyses of a sample, e.g., orange oil, on an unlocked GC system, can result in substantial variations in relative retention times of analytes, thereby generating varying patterns of peaks, and possibly leading to changes in elution order of sample components. Such results typically occur if the relationship of temperature program rate to flow rate of the GC system is not maintained. FIG. 7, depicts the chromatograms of FIG. 6 after realignment of the peaks using traditional mathematical scaling techniques, e.g., offset and span adjustment. Note that not all peak maxima fall within their targeted time windows (windows 702, 704, 706 and 708) even after adjustment, and that the adjustment could not correct for changes in the elution profiles that occurred due to unlocked conditions. Thus, if one attempts to align chromatograms with traditional mathematical scaling techniques, the errors in relative retention typically remain.

Figure 8:
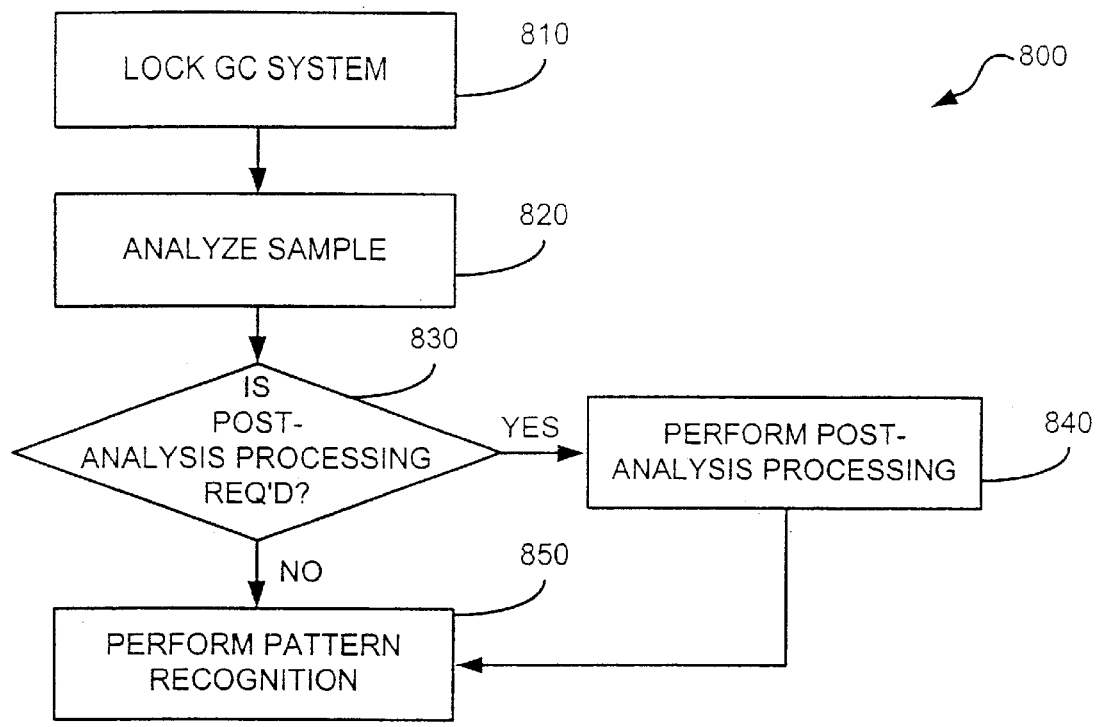
FIG. 8 is a flow diagram depicting the functionality of a preferred method of the present invention.

As shown in FIG. 8, a preferred method 800 of the present invention includes the step (block 810) of locking a GC system to parameters embodied in a fingerprint database (retention-time type or retention-factor type, described hereinbefore). At block 820, the sample is then analyzed in accordance with conventional procedures, resulting in the acquisition of chromatographic data relating to the sample. Proceeding to block 830, a determination then is made as to whether post-analysis processing of the acquired data is required. If such processing is required, the method may proceed to block 840 where the desired processing, such as mathematical scaling, for example, is applied to the data. After block 840 or, alternatively, if it is determined in block 830 that no post-analysis processing is required, the method may proceed to block 850 where pattern recognition is performed.

The preferred method of the present invention described herein may be utilized on numerous chromatographic systems, such as a system incorporating a computing apparatus, i.e., computing apparatus 106 of FIG. 1, which has an appropriate database of chromatographic fingerprints (fingerprint database) and/or chemometric model stored in memory, i.e., memory 108. In such embodiments, chemometric techniques may be applied to the data locally so that a representative characteristic, such as the classification, identification, etc., of the sample may be determined.

Figure 9:
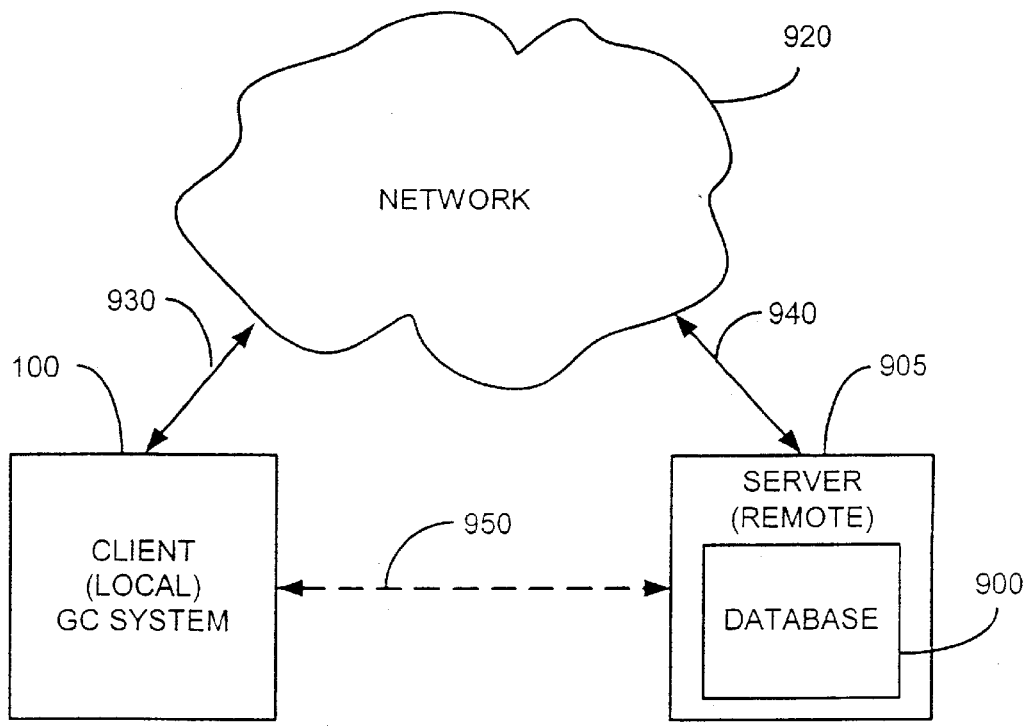
FIG. 9 is a schematic diagram depicting a preferred method of the present invention.

In an alternative embodiment (FIG. 9), the appropriate fingerprint database and/or chemometric model 900 may be stored in the memory of a remote server 905. So configured, chromatographic data may be obtained from a local GC system, such as GC system 100, with the raw chromatographic data or post-analysis processed chromatographic data then being provided to the server, or other remote computing apparatus, for chemometric processing. As depicted in FIG. 9, server 905 is preferably linked to GC system 100 through the use of a network 920, i.e., Internet, Intranet, Ethernet, etc., via links 930 and 940. Additionally, in some embodiments, GC system 100 may be linked directly to the server, such as via link 950 so that utilization of a network 920 is not necessary. Preferably, once the server 900 receives the chromatographic data from GC system 100, chemometric techniques may be applied to the data, with any achieved results being accessible at the server by the GC system 100.

Through the use of such an accessible database and/or server implemented with chemometrics functionality, processing and storage of chromatographic data may be facilitated, i.e., facilitated remotely from the data-gathering components of the GC system. So provided, the chemometrics functionality implemented may be simultaneously accessed by a plurality of users, such as by users working in a field environment. Additionally, the various fingerprint databases, chemometric models and data processing algorithms of the system may be conveniently updated so as to provide an effective system for performing one or more of a variety of functions, including: preprocessing of chromatographic data; chemometric analysis; archiving of data, and; dissemination of data, among others.

Figure 10:
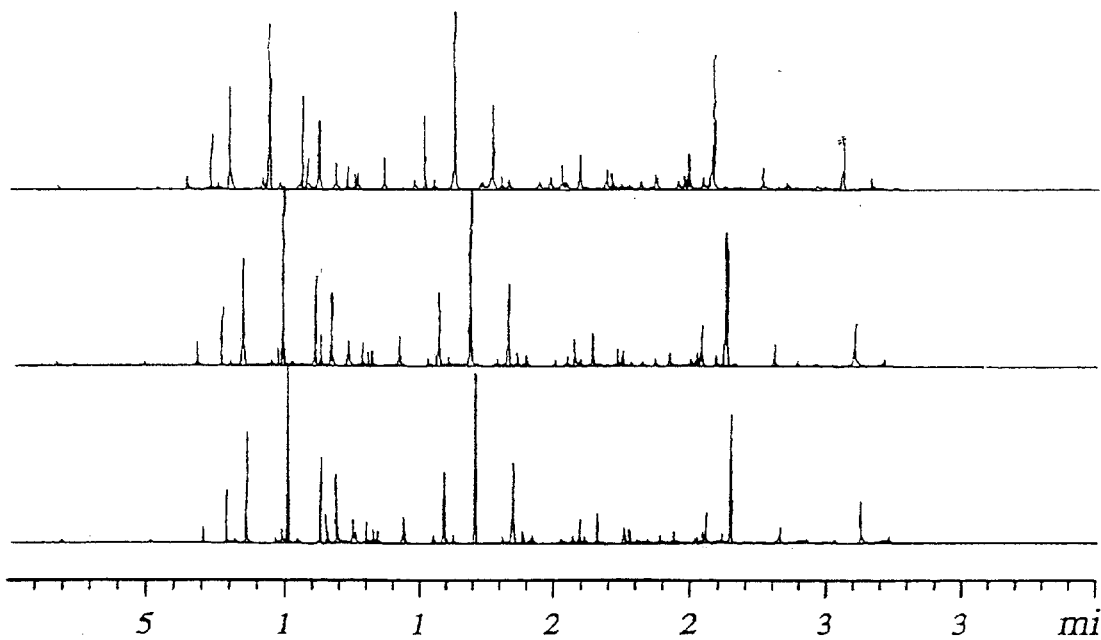
FIG. 10 depicts representative chromatograms generated by unlocked GC systems.
Figure 11:
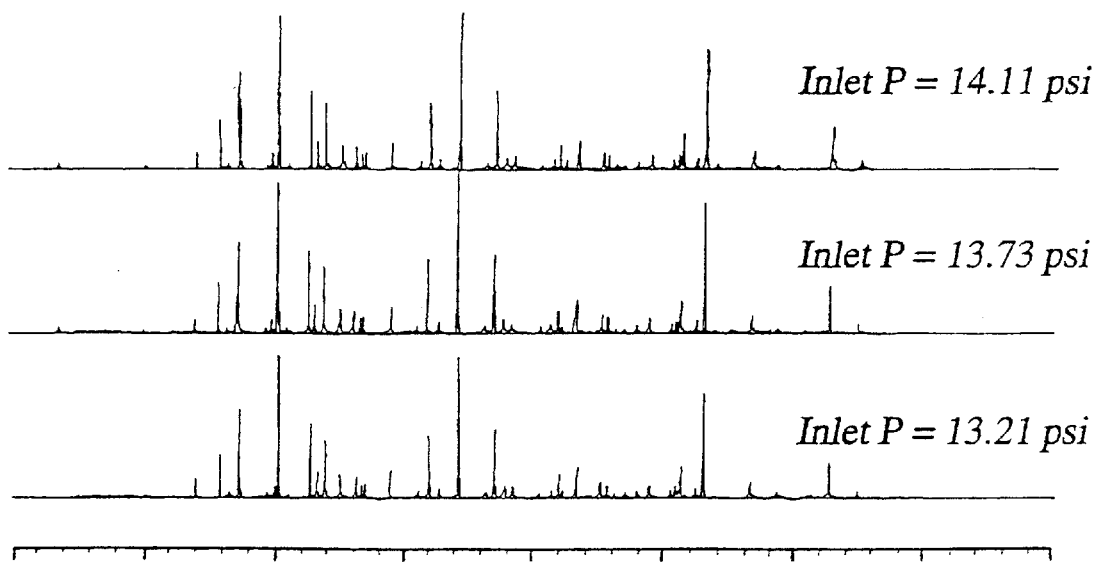
FIG. 11 depicts representative chromatograms generated by locked GC systems.

Through the application of the present invention, peaks elute from the chromatograph at matched retention times and, necessarily, with the correct relative retention. Representative advantages of the present invention are illustrated in FIGS. 10 and 11. For example, as depicted in FIG. 10, replicate analyses of a sample, e.g., a fragrance sample A, were conducted on three different GC systems, with the systems not being locked. The misalignment of peaks and shifts in relative retention among the analyses degrade the accuracy of subsequently applied pattern recognition techniques. As depicted in FIG. 11, however, replicate analyses of fragrance sample A were conducted on three different GC systems, with the systems locked (as described hereinbefore), thereby ensuring alignment of retention times and peak elution order. So provided, improved alignment and peak elution order improve pattern recognition techniques. Moreover, when chromatographic data is collected under retention time locked conditions, further mathematical alignment is usually unnecessary prior to pattern classification.

The foregoing description has been presented for purposes of illustration and description. It is not intended to be exhaustive or to limit the invention to the precise forms disclosed. Obvious modifications or variations are possible in light of the above teachings. The embodiment or embodiments discussed, however, were chosen and described to provide the best illustration of the principles of the invention and its practical application to thereby enable one of ordinary skill in the art to utilize the invention in various embodiments and with various modifications as are suited to the particular use contemplated. All such modifications and variations, are within the scope of the invention as determined by the appended claims when interpreted in accordance with the breadth to which they are fairly and legally entitled.

What is claimed is:

1. A method for chromatographically analyzing a sample based upon a reference GC system operated under locked conditions, the reference GC system having a GC column operated at a column head pressure, and having a defined retention time and a defined column void time corresponding to a known analyte, said method comprising the steps of:

providing a locking GC system having a column operated at a column head pressure;

adjusting the column head pressure of the locking GC system such that a column void time of the column in the locking GC system, when the known analyte is eluted therethrough, is matched with the column void time of the column in the reference GC system, when the known analyte is eluted therethrough, or by adjusting the column head pressure of the locking GC system such that a retention time of the known analyte in the column of the locking GC system is matched with the retention time of the known analyte in the column of the reference GC system;

analyzing the sample with the locking GC system such that chromatographic data corresponding to the sample is compiled; and performing chemometric analysis on the chromatographic data;

wherein the reference GC system was operated under locked conditions to generate a fingerprint database;

wherein the step of performing chemometric analysis comprises performing pattern recognition by interpreting the chromatographic data in relation to the fingerprint database such that a characteristic of the sample is determined;

wherein the locking GC system has a computing apparatus associated therewith, the computing apparatus having a memory storage device, the fingerprint database residing in the memory storage device, and wherein the step of interpreting the chromatographic data comprises accessing the fingerprint database residing in the memory storage device.

2. The method of claim 1, wherein the step of analyzing the sample with the locking GC system comprises the step of mathematically scaling the chromatographic data.

3. The method of claim 1, wherein the step of performing chemometric analysis comprises interpreting the chromatographic data in relation to a chemometric model such that a characteristic of the sample is determined.

4. The method of claim 1, wherein the fingerprint database is a retention time database.

5. The method of claim 1, wherein the fingerprint database is a retention factor database.

6. A method for chromatographically analyzing a sample based upon a reference GC system operated under locked conditions, the reference GC system having a GC column operated at a column head pressure, and having a defined retention time and a defined column void time corresponding to a known analyte, said method comprising the steps of:

providing a locking GC system having a column operated at a column head pressure;

adjusting the column head pressure of the locking GC system such that a column void time of the column in the locking GC system, when the known analyte is eluted therethrough, is matched with the column void time of the column in the reference GC system, when the known analyte is eluted therethrough, or by adjusting the column head pressure of the locking GC system such that a retention time of the known analyte in the column of the locking GC system is matched with the retention time of the known analyte in the column of the reference GC system;

analyzing the sample with the locking GC system such that chromatographic data corresponding to the sample is compiled; and performing chemometric analysis on the chromatographic data;

wherein the reference GC system was operated under locked conditions to generate a fingerprint database;

wherein the step of performing chemometric analysis comprises performing pattern recognition by interpreting the chromatographic data in relation to the fingerprint database such that a characteristic of the sample is determined;

wherein the fingerprint database resides in a memory storage device of a remote server, and wherein the step of interpreting the chromatographic data comprises the steps of:

accessing the remote server via a communications network; and providing the chromatographic data to the remote server.

7. The method of claim 6, wherein the reference GC system was operated under locked conditions to generate a fingerprint database, and wherein the step of performing chemometric analysis comprises performing pattern recognition by interpreting the chromatographic data in relation to the fingerprint database such that a characteristic of the sample is determined.

8. The method of claim 6, wherein the step of analyzing the sample with the locking GC system comprises mathematically scaling the chromatographic data.

9. The method of claim 6, wherein the step of performing chemometric analysis comprises interpreting the chromatographic data in relation to a chemometric model such that a characteristic of the sample is determined.

10. The method of claim 6, wherein the fingerprint database is a retention time database.

11. The method of claim 6, wherein the fingerprint database is a retention factor database.

12. A method for chromatographically analyzing a sample based upon a reference GC system operated under locked conditions, the reference GC system having a GC column operated at a column head pressure, and having a defined retention time and a defined column void time corresponding to a known analyte, said method comprising the steps of:

providing a locking GC system having a column operated at a column head pressure;

adjusting the column head pressure of the locking GC system such that a column void time of the column in the locking GC system, when the known analyte is eluted therethrough, is matched with the column void time of the column in the reference GC system, when the known analyte is eluted therethrough, or by adjusting the column head pressure of the locking GC system such that a retention time of the known analyte in the column of the locking GC system is matched with the retention time of the known analyte in the column of the reference GC system;

analyzing the sample with the locking GC system such that chromatographic data corresponding to the sample is compiled; and performing chemometric analysis on the chromatographic data;

wherein the step of performing chemometric analysis comprises interpreting the chromatographic data in relation to a chemometric model such that a characteristic of the sample is determined;

wherein the locking GC system has a computing apparatus associated therewith, the computing apparatus having a memory storage device, and wherein the chemometric model resides in the memory storage device.

13. The method of claim 12, wherein the step of analyzing the sample with the locking GC system comprises mathematically scaling the chromatographic data.

14. The method of claim 12, wherein the reference GC system was operated under locked conditions to generate a fingerprint database, and wherein the step of performing chemometric analysis comprises performing pattern recognition by interpreting the chromatographic data in relation to the fingerprint database such that a characteristic of the sample is determined.

15. The method of claim 12, wherein the fingerprint database is a retention time database.

16. The method of claim 12, wherein the fingerprint database is a retention factor database.

17. A method for chromatographically analyzing a sample based upon a reference GC system operated under locked conditions, the reference GC system having a GC column operated at a column head pressure, and having a defined retention time and a defined column void time corresponding to a known analyte, said method comprising the steps of:

providing a locking GC system having a column operated at a column head pressure;

adjusting the column head pressure of the locking GC system such that a column void time of the column in the locking GC system, when the known analyte is eluted therethrough, is matched with the column void time of the column in the reference GC system, when the known analyte is eluted therethrough, or by adjusting the column head pressure of the locking GC system such that a retention time of the known analyte in the column of the locking GC system is matched with the retention time of the known analyte in the column of the reference GC system;

analyzing the sample with the locking GC system such that chromatographic data corresponding to the sample is compiled; and performing chemometric analysis on the chromatographic data;

wherein the step of performing chemometric analysis comprises interpreting the chromatographic data in relation to a chemometric model such that a characteristic of the sample is determined;

wherein the chemometric model resides in a memory storage device of a remote server, and wherein the step of interpreting the chromatographic data comprises the steps of:

accessing the remote server via a communications network; and providing the chromatographic data to the remote server.

18. The method of claim 17, wherein the step of analyzing the sample with the locking GC system comprises mathematically scaling the chromatographic data.

19. The method of claim 17, wherein the reference GC system was operated under locked conditions to generate a fingerprint database, and wherein the step of performing chemometric analysis comprises performing pattern recognition by interpreting the chromatographic data in relation to the fingerprint database such that a characteristic of the sample is determined.

20. The method of claim 17, wherein the fingerprint database is a retention time database.

21. The method of claim 17, wherein the fingerprint database is a retention factor database.

22. A method for chromatographically analyzing a sample based upon a reference GC system operated under locked conditions, the reference GC system having a GC column operated at a column head pressure, and having a defined retention time and a defined column void time corresponding to a known analyte, said method comprising the steps of:

receiving chromatographic data from a locking GC system, the locking GC system having a column operated at a column head pressure which is adjusted such that a column void time of the column in the locking GC system, when the known analyte is eluted therethrough, is matched with the column void time of the column in the reference GC system, when the known analyte is eluted therethrough, or is adjusted such that a retention time of the known analyte in the column of the locking GC system is matched with the retention time of the known analyte in the column of the reference GC system, the chromatographic data corresponding to the sample; and performing chemometric analysis on the chromatographic data;

wherein the reference GC system was operated under locked conditions to generate a fingerprint database, and wherein the step of performing chemometric analysis comprises performing pattern recognition by interpreting the chromatographic data in relation to the fingerprint database such that a characteristic of the sample is determined;

wherein the fingerprint database resides in a memory storage device of a remote server, and wherein the step of receiving chromatographic data comprises receiving chromatographic data at the remote server via a communications network.

23. The method of claim 22, wherein the step of performing chemometric analysis comprises interpreting the chromatographic data in relation to a chemometric model such that a characteristic of the sample is determined.

24. The method of claim 22, wherein the fingerprint database is a retention time database.

25. The method of claim 22, wherein the fingerprint database is a retention factor database.

26. A method for chromatographically analyzing a sample based upon a reference GC system operated under locked conditions, the reference GC system having a GC column operated at a column head pressure, and having a defined retention time and a defined column void time corresponding to a known analyte, said method comprising the steps of:

receiving chromatographic data from a locking GC system, the locking GC system having a column operated at a column head pressure which is adjusted such that a column void time of the column in the locking GC system, when the known analyte is eluted therethrough, is matched with the column void time of the column in the reference GC system, when the known analyte is eluted therethrough, or is adjusted such that a retention time of the known analyte in the column of the locking GC system is matched with the retention time of the known analyte in the column of the reference GC system, the chromatographic data corresponding to the sample; and performing chemometric analysis on the chromatographic data;

wherein the step of performing chemometric analysis comprises interpreting the chromatographic data in relation to a chemometric model such that a characteristic of the sample is determined;

wherein the chemometric model resides in a memory storage device of a remote server, and wherein the step of receiving chromatographic data comprises receiving chromatographic data at the remote server via a communications network.

27. The method of claim 26, wherein the reference GC system was operated under locked conditions to generate a fingerprint database, and wherein the step of performing chemometric analysis comprises performing pattern recognition by interpreting the chromatographic data in relation to the fingerprint database such that a characteristic of the sample is determined.

28. The method of claim 26, wherein the step of analyzing the sample with the locking GC system comprises mathematically scaling the chromatographic data.

29. The method of claim 26, wherein the fingerprint database is a retention time database.

30. The method of claim 26, wherein the fingerprint database is a retention factor database.

31. A method for chromatographically analyzing a sample based upon a reference GC system operated under locked conditions to generate a retention factor database, the reference GC system having a GC column operated at a column head pressure, and having a defined retention time and a defined column void time corresponding to a known analyte, said method comprising the steps of:

providing a locking GC system having a column operated at a column head pressure;

adjusting the column head pressure of the locking GC system such that a column void time of the column in the locking GC system, when the known analyte is eluted therethrough, is matched with the column void time of the column in the reference GC system, when the known analyte is eluted therethrough, or by adjusting the column head pressure of the locking GC system such that a retention time of the known analyte in the column of the locking GC system is matched with the retention time of the known analyte in the column of the reference GC system;

analyzing the sample with the locking GC system such that chromatographic data corresponding to the sample is compiled; and performing chemometric analysis comprises performing pattern recognition by interpreting the chromatographic data in relation to the retention factor database such that a characteristic of the sample is determined.

32. The method of claim 31, wherein the step of analyzing the sample with the locking GC system comprises mathematically scaling the chromatographic data.

33. The method of claim 31, wherein the reference GC system was operated under locked conditions to generate a fingerprint database, and wherein the step of performing chemometric analysis comprises performing pattern recognition by interpreting the chromatographic data in relation to the fingerprint database such that a characteristic of the sample is determined.

34. The method of claim 31, wherein the step of performing chemometric analysis comprises interpreting the chromatographic data in relation to a chemometric model such that a characteristic of the sample is determined.

* * * * *